(12) United States Patent
Baba et al.

(10) Patent No.: US 6,489,609 B1
(45) Date of Patent: Dec. 3, 2002

(54) ION TRAP MASS SPECTROMETRY AND APPARATUS

(75) Inventors: Takashi Baba, Hatoyama (JP); Izumi Waki, Asaka (JP); Dongbing Wang, Hatoyama (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 09/517,175

(22) Filed: Mar. 2, 2000

(30) Foreign Application Priority Data

May 21, 1999 (JP) ............................................ 11-142128

(51) Int. Cl.[7] ................................................. H01J 49/42
(52) U.S. Cl. ........................ 250/282; 250/281; 250/288; 250/292
(58) Field of Search ................................. 250/281, 251, 250/288, 282, 292, 290, 291, 293

(56) References Cited

U.S. PATENT DOCUMENTS 5,274,232 A * 12/1993 Chu et al. .................... 250/251
5,679,950 A * 10/1997 Baba et al. ................... 250/281
6,101,203 A * 8/2000 Yamamoto et al. ............ 372/39

OTHER PUBLICATIONS

H. Dehmelt, "Radiofrequency Spectroscopy of Stored Ions I: Storage", *Advances in Atomic and Molecular Physics*, vol. 3, 1967, pp. 53–72, ISSN 0065–2199, Academic Press.

R. March et al., "Quadrupole Storage Mass Spectrometry", *Chemical Analysis: A Series of Monographs on Analytical Chemistry and Its Applications*, vol. 102, 1989, pp. xiii–xx (Contents), ISSN 0069–2883, John Wiley & Sons.

* cited by examiner

Primary Examiner—John R. Lee
Assistant Examiner—David A. Vanore
(74) Attorney, Agent, or Firm—Antonelli, Terry, Stout & Kraus, LLP

(57) ABSTRACT

A laser-cooled fluorescence mass spectrometry and device thereof capable of non-destructive analysis with acquiring a strong signal intensity by separating the laser cooling means and the ion temperature probe means.

12 Claims, 14 Drawing Sheets

ION TRAP MASS SPECTROMETRY AND APPARATUS

BACKGROUND OF THE INVENTION

Field of the Invention

The present invention relates to a method and apparatus therefor, for an improved laser-cooling fluorescence spectrometry as one type of ion trapping mass spectrometry.

Ion trapping mass spectrometry is a widely used method for trace analysis in environmental analysis and other fields. In the most typically utilized method, ions trapped in an ion trap are subjected to mass selection and extracted outside the trap, and these extracted ions are detected with an ion detector such as an electron multiplier. This type of mass spectrometry is still the most widely used method and a large number of reference works are available (such as Reference 1: R. E. March and R. J. Hughes: "Quadrupole Storage Mass Spectrometry" John Wiley and Sons (1989)).

Laser-cooled fluorescence mass spectrometry relating to this invention is found in a method disclosed in 1995 (Reference 2: U.S. Pat. No. 5,679,950) as a novel ion trap mass spectrometry. In this method, laser-cooling and sympathetic cooling are utilized and sensitivity which has been limited to detection levels of about 100 ions in the ion trapping mass spectrometry of the prior art, is significantly improved by optical detection of the cooled sample ions so that even single ions can be detected in-situ. In this method, the sample ions are trapped in the ion trap after mass analysis and can be measured repeatedly to detect ions in an "in-situ" (or non-destructive) manner.

SUMMARY OF THE INVENTION

The principle of laser-cooled fluorescence mass spectrometry is briefly described below.

Ions trapped in a radio-frequency-quadrupole ion trap possess a harmonic oscillation mode due to the potential of the ion trap (in pseudo-potential approximation). The oscillation of these trapped ions is known as secular (oscillation) motion. The frequencies of these secular oscillations are proportional to the charge of the ions and are inversely proportional to the mass. If the secular frequency can be detected, then the mass spectrometry of the ions can be performed (Reference 1).

Firstly, the laser-cooled ions and sample ions are simultaneously trapped and cooled. The sample ions are sympathetically cooled by the laser-cooled ions. Next, an electrical oscillation is applied to make the sample ions resonate at the secular frequency, so that the sample ions are heated by the resonant oscillation. The sample ions are repeatedly undergoing Coulomb collision with the laser-cooled ions so that the sample ions transfer energy to the laser-cooled ions and the laser-cooled ions are sympathetically heated.

Increase of the temperature of the laser-cooled ions results in such effects as change of the fluorescence intensity, and change in the spatial distribution of the fluorescence. These changes give information on the mass and the amount of the sample ions.

The mechanism of fluorescence intensity change in the laser-cooled fluorescence mass spectrometry can be understood by the following brief theoretical analysis.

First, using a simplified theory of Doppler laser-cooling, the relation of laser cooling efficiency and fluorescence intensity is calculated with respect to ion temperature.

When a laser beam with a fixed wave vector irradiates free atoms (or ions), a force acts on the atoms in the direction of the wave vector of the light due to photon scattering. Laser cooling is performed using this force. Typically, an atom having a simple two-level transition is chosen to avoid optical pumping, and the laser wavelength is adjusted to the resonance transition of the two-level atom species.

When the momentum of the atom is counter to the direction of the wave vector of the laser light, the velocity of the atoms decreases after resonant absorption of photons due to momentum transfer of photons to the atom. Conversely, when the momentum of the atom is in the same direction of the wave vector of the laser light, then the velocity increases.

When the detuning frequency is negative, in other words, when the light has a wavelength slightly longer than the resonant wavelength, the probability of resonance scattering increases when the atoms are traveling counter to the direction of laser light wave vector, compared to when traveling in the same direction to the light wave vector due to the Doppler effect. In this case, consequently, the energy of the atom is lost and the atom cools down.

Spatially-uniform natural emission following absorption results in a random-walk increase of energy, whose balance with the cooling effect determines the ultimate attainable temperature h $\Gamma$/2, where $\Gamma$ is the natural linewidth of the transition. As shown below, the average energy change due to resonant absorption is h $\Delta v$, where $\Delta v$ is the detuning frequency, which is the deviation of the laser light frequency from the resonant frequency $v_0$ of the atoms at rest. When |h $\Delta v$| is greater than h $\Gamma$/2, we can neglect the random-walk heating by natural emission, which is the case considered below to simplify discussion.

An average energy change h $\Delta v$ due to resonance absorption of photons can be explained by simple kinetics. The wave vector direction of the laser light is set as the z axis. The velocity component along the z axis of the atom with mass m is defined as $v_z$ in the laboratory frame. In the center of mass system, the frequency of the light shifts $v(1-v_z/C)$ due to the Doppler effect. When $v(1-v_z/C)$ matches the resonant frequency $v_0$, a resonant scattering occurs. The atom obtains momentum h $v_0$/c from the laser light when the atom absorbs the light. Next, the atom emits photon by spontaneous emission process. This photon emission is uniform in all directions so net average change of the atom momentum does not occur. Consequently, the atom obtains momentum h $v_0$/C by the resonant scattering of the laser light.

The velocity after the resonant scattering becomes $v_z'$= $v_z$+h $v_0$/mc when observed in the laboratory frame. The change $\Delta E$ of kinetic energy is $$\Delta E = \frac{mv_z'^2}{2} - \frac{mv_z^2}{2} \quad \text{(Equation 1)}$$

$$= h\Delta v\left(1 + \frac{h\Delta v}{4E}\right)$$

$$\cong h\Delta v$$

When the atom is in the laser beam, the rate of resonant scattering per unit time is given by $$sr(v_z, I) = \frac{\Gamma \Omega_{rabi}^2}{\left(v - v_0 - \frac{vv_z}{c}\right)^2 + \Gamma^2 + \Omega_{rabi}^2} \quad \text{(Equation 2)}$$

Here, $\Gamma$ is the natural width of the transition. $\Omega_{Rabi}$ is the Rabi frequency, which depends on the light intensity.

Using these relations, an atom with velocity $v_z$ attains an energy change per unit time $\Delta E_{scatt}$ due to the resonant scattering;

$$\left(\frac{\Delta E_{scatt}}{\Delta t}\right)(v_z, I, \Delta v) = h\Delta v \, \text{sign}(v_z) sr(v_z, I) \quad \text{(Equation 3)}$$

Here, sign ($V_z$) is a symbol that indicates the direction of the motion of the atom relative to the laser beam. It is negative when the directions of the atom and light beam are opposite, in which case the atom slows down. It is positive when the directions are the same, in which case the atom accelerates.

Next, the average energy and fluorescence intensity is calculated when laser-cooling is applied to the ions. Here, it is assumed that the ions are in a gaseous state (not in a Wigner-crystal state). The velocity distribution n $(v_x, v_y, v_z)$ can be written as a Maxwell distribution with an ion temperature T;

$$n(v_x, v_y, v_z) = N\left(\frac{m}{2\pi kT}\right)^{\frac{3}{2}} \exp\left(-m\frac{v_x^2 + v_y^2 + v_z^2}{2kT}\right) \quad \text{(Equation 4)}$$

Modifying this equation to one-dimension, the laser cooling efficiency, which is defined as the average energy change of an ion by laser-cooling per unit time, can be described as $$\left(\frac{m}{2\pi kT}\right)^{\frac{1}{2}} \int \left(\frac{\Delta E_{scatt}}{\Delta t}\right)(v_z, I, \Delta v) \exp\left(-m\frac{v_z^2}{2kT}\right) dv_z \quad \text{(Equation 5)}$$

The fluorescence intensity per unit time of an ion with temperature T, averaged over the velocity distribution, is $$\left(\frac{m}{2\pi kT}\right)^{\frac{1}{2}} \int sr(I, v_z) \exp\left(-m\frac{v_z^2}{2kT}\right) dv_z \quad \text{(Equation 6)}$$

In laser-cooled fluorescence mass spectrometry, an alternating-current electrical field is applied to excite the secular motion of the sample ions. The maximum heating rate by this AC electric field, which is defined as the maximum value of the energy increase $\Delta E_{heat}$ per unit time, can be described as $$\left(\frac{\Delta E_{heat}}{\Delta t}\right)_{max} = \left(\frac{2kT}{\pi m}\right)^{\frac{1}{2}} \frac{eV_{ac}}{8r_0} \quad \text{(Equation 7)}$$

where T is the ion temperature, $V_{ac}$ is the voltage amplitude of dipole AC electrical field applied to the electrodes. Hereafter, Equation 7 is derived.

A precise calculation of the actual heating rate (or the change of temperature) of the ions might not be simple because the Coulomb interaction between ions constitutes a many-body non-linear system, and because a precise calculation must include laser-cooling effect at the same time, which also depends non-linearly on the ion velocity. On the other hand, to determine a suitable set of operation parameters for the laser-cooled fluorescence mass spectroscopy, an approximate knowledge of the maximum heating rate in the absence of laser-cooling is quite useful as will be discussed later. Thus, we attempt to find the maximum upper limit for the heating rate under the following conditions:

(a) there is no laser cooling,
(b) applied AC oscillation frequency $\omega$ matches the secular motion oscillation $\omega_0$, and
(c) Coulomb interaction between ions is ignored.

That is, heating due to the trapping radio-frequency is ignored, since it is much smaller than the resonant forced-oscillation heating.

Further, we assume the equation of motion as a one-dimensional forced oscillation without damping:

$$\frac{d^2 x}{dt^2} = \frac{f}{m}\exp(i\omega t) - \omega_0^2 x \quad \text{(Equation 8)}$$

where f is the amplitude of the force. In the present case, AC electric voltage $V_{ac}$ is applied to two pairs of adjacent quadrupole electrodes, resulting in an approximate oscillating electric field amplitude $f=eV_{ac}/(2r_0)$.

When Equation 8 is solved for velocity v with initial conditions v(t=0)=0 and x(t=0)=0, $$v = \frac{ft}{2m}\cos(\omega_0 t) = v_0 \cos(\omega_0 t) \quad \text{(Equation 9)}$$

where $v_0 = ft/2$ m.

The energy E at time t is given by $$E = \frac{1}{4}mv_0^2 = \frac{f^2}{16m}t^2 \quad \text{(Equation 10)}$$

Extending this result, we approximate the heating rate of any ion at velocity $V_0$ by $$\frac{dE}{dt} = \frac{f^2}{8m}t = \frac{f}{4}v_0 \quad \text{(Equation 11)}$$

Assuming a Maxwellian distribution of ion velocity $V_0$ with temperature T, the maximum heating rate is approximated by $$\frac{\Delta E_{heat}}{\Delta t_{max}} = \left(\frac{m}{2\pi kT}\right)^{\frac{1}{2}} \int \frac{dE}{dt} \exp\left(\frac{-mv_0^2}{2kT}\right) dv_0 \quad \text{(Equation 12)}$$

$$= \left(\frac{2kT}{\pi m}\right)^{\frac{1}{2}} \frac{eV_{ac}}{8r_0}$$

FIG. 4 through FIG. 8 show calculated results of the temperature dependence of the laser cooling rate (or, cooling efficiency) of a typical laser-cooled ion $^{24}Mg^+$ at various laser beam parameters. Each figure includes curves for various values of the detuning frequency. The horizontal axis shows the ion temperature. The vertical axis shows the laser-cooling rate. The laser-cooling rate has a maximum cooling rate at temperatures between about 1 and 100 K.

The figures also show the temperature dependence of the maximum heating rate at various values of analysis voltage $V_{ac}$. The vertical axis shows the maximum heating rate. The laser beam, which is focused to a diameter of 0.2 mm, has a power of 1 $\mu$W, 10 $\mu$W, 100 $\mu$W, 1 mW and 10 mW, respectively in each figure.

FIG. 9 through FIG. 13 show calculations of the temperature dependence of the fluorescence intensity of $^{24}Mg^+$ ions at various laser beam parameters. Each figure includes curves for various values of the detuning frequency. The horizontal axis shows the ion temperature. The vertical axis shows the fluorescence intensity. The figures respectively shows results for laser beams of 1 $\mu$W, 10 $\mu$W, 100 $\mu$W, 1 mW and 10 mW focused to a diameter of 0.2 mm.

FIG. 14 through FIG. 17 show calculated results of the temperature dependence of the laser cooling rate of a typical laser-cooled ion $^{138}Ba^+$ at various laser beam parameters. The figures also show the temperature dependence of the maximum heating rate at various values of analysis voltage $V_{ac}$. FIG. 18 through FIG. 21 show calculations of the temperature dependence of the fluorescence intensity of $^{138}Ba^+$ ions at various laser beam parameters.

The following data are used in the calculations.

Mass of $^{24}Mg^+$ - - - m=24 $m_u$
Resonance wavelength of $^{24}Mg^+$ - - - $\lambda_0$=280 nm
Natural width of $^{24}Mg^+$ - - - $\Gamma$=43 MHz
Mass of $^{138}Ba^+$ - - - m=138 $m''$
Resonant wavelength of $^{138}Ba^+$ - - - $-\lambda_0$=493 nm
Natural width of $^{138}Ba^+$ - - - $\Gamma$=15.1 MHz In the calculations of $^{138}Ba^+$, it is treated as a 2-level atom, where the pump-back transition is ignored, and only the laser-cooling transition of $^{138}Ba^+$ is taken into account.

The above calculations give insight on the mechanism of how the mass-signal is produced in laser-cooled fluorescence mass spectrometry, and teaches us a valuable guidance on how to stably obtain the signal.

Firstly, the mechanism of the signal generation is considered from the relation between ion temperature and fluorescence intensity.

We consider the case of $\Omega_{Rabi} \leq \Gamma$, where the resonance scattering is not strongly saturated. At detuning frequency smaller than natural width of the transition, the fluorescence intensity increases when the ions are laser-cooled and drop its temperature. (See for instance, the characteristic for a detuning frequency from 0 to 40 MHz in FIG. 9.). We observe this typical effect when laser cooling experiments are performed. When the detuning frequency becomes much larger than the natural linewidth, the fluorescence intensity reaches an maximum value at temperature around one to ten Kelvin (See for instance the characteristic in FIG. 9 when the detuning frequency is larger than −50 MHz.) This maximum occurs because the probability of absorbing laser light becomes larger with a wider velocity distribution due to the Doppler effect.

Next, we explain the case of $\Omega_{Rabi} >> \Gamma$, where the resonance scattering is strongly saturated. Though a strong fluorescence intensity could be obtained by causing saturation, the dependence of fluorescence intensity on ion temperature and detuning frequency became smaller (See for instance, the characteristic of FIG. 12 and FIG. 13.). This effect appears because the width of resonant absorption spectra widens due to saturation, so that the resonance scattering rate does not depend so much on the ion velocity at small detuning frequencies.

In laser-cooled fluorescence mass spectrometry, information on changes of temperature is obtained from the changes in fluorescence intensity. For maximum signal, it is necessary to maximize the change of fluorescence. Above arguments teach us that, to this end, it is desirable to keep the laser power low enough not to saturate the transition, and to keep the detuning to zero.

Next, we discuss the conditions for maintaining nondestructive analysis using the relation between ion temperature and laser cooling rate.

In our calculation, the laser-cooling rate has a maximum cooling rate at temperatures between about 0.1 K and 100 K when $\Omega_{Rabi} < \Gamma$. At lower temperature, the cooling rate decreases as the temperature decreases. The laser cooling rate approaches zero as the temperature decreases, because, in our approximation, the decrease of the width of the Doppler velocity distribution results in the decrease of mean energy loss due to photon absorption. In reality, as the temperature approaches zero, the heating effect from natural emission of photons by excited ions must be taken into account, whose balance with the cooling effect by photon absorption will determine the lowest temperature attainable. Since the temperature in our calculation is much higher than the temperature where such a heating by natural emission becomes important, we considered only the cooling effect by absorption.

Above the maximum cooling rate, the rate drops as the temperature rises. At higher temperatures, the laser cooling rate decreases due to decreased probability of photon absorption.

We now describe ion stability in laser-cooled fluorescence mass spectrometry, using these calculation of the laser cooling rate and the maximum heating rate by the forced oscillation. Ion loss may occur when the maximum heating rate is larger than the laser cooling rate.

When the sample ions are oscillated by external fields, the heating rate is proportional to the number of sample ions, and the cooling rate is proportional to the number of laser-cooled ions. The heat coupling between the laser-cooled ions and the sample ions depends on the sympathetic cooling rate. In the following typical calculation, the number of ions is set equal to the number of laser-cooled ions, and the calculation assumes that the sympathetic coupling is complete, i.e., that there is no temperature difference between the sample ions and the laser-cooled ions.

When the maximum heating rate from heating (hereafter, analysis heating) due to the forced oscillation of the ion by the analysis voltage is smaller than the laser cooling rate, ions are not lost due to analysis, and are stable. At a fixed set of values of the analysis-voltage amplitude and laser beam parameters, the intersection of the maximum-heating-rate line and the laser-cooling curve provides a guide for establishing the temperature where the cooling and heating are balanced. Of the two intersections that may exist, the intersection on the lower temperature side provides a guide for the ion temperature during analysis heating. If the heating rate due to analysis heating at this ion temperature is increased by increasing the analysis voltage, the ion temperature shifts to a higher value. When the analysis voltage is further increased, the maximum heating rate line and the laser cooling line come in contact at a single point. See, for instance, the contact made by the line for analysis voltage 0.9 mV in FIG. 4 and the line for the detuning frequency −30 MHz. This point yields the maximum temperature that can be stably reached under that specific laser cooling conditions. When a larger analysis voltage is applied to provide further heating, the analysis heating rate exceeds the laser cooling rate, so that the ions are heated at any temperature without reaching a stable balance with cooling, and ions are lost. That is, an upper limit for analysis voltage exists at a fixed laser-cooling condition where analysis is performed without losing ions. Hereafter, this temperature is referred to as the maximum ion temperature, and is shown by the white circles in the FIGS. 4–8, FIGS. 14–17, FIG. 22, and FIG. 23.

Therefore, in laser-cooled fluorescence mass spectrometry as shown above, by applying cooling that is stronger than the applied forced-oscillation, the laser-cooled ions and sample ions can be trapped stably in the ion trap. Preferably, parameters should be chosen so that strong and stable cooling is realized over as wide an ion temperature range as possible in the presence of temperature increase due to analysis heating. The present calculations show that, for effective and stable cooling, the intensity of the laser beam should preferably be so strong as to saturate the transition, and the laser detuning should preferably be much larger than the natural linewidth of the transition. The extent of saturation of the intensity should not be so strong as to lowering the laser-cooling efficiency itself.

We point out two issues in the laser-cooled fluorescence mass spectrometry of the prior art. One issue is that finding the laser cooling conditions for obtaining a signal is difficult in general. For instance, when the number of ions changes, then new conditions must be searched for. Another issue is that even if conditions are found for obtaining a signal, loss of ions in the trap frequently occurs due to analysis heating.

As shown before, in-situ (in-trap) analysis can be performed in principle in the spectrometry of the prior art. However, to make in-trap analysis possible, a plurality of strict optimal parameters are required. If optimal conditions are not provided, then the ions are lost, or no signal can be obtained. Since selecting the correct analysis parameters is difficult, considerable experience is needed to implement the spectrometry of the prior art.

The intent of this invention is to overcome these two issues of the prior art. In the prior art, these two issues arise because one species of ions is simultaneously used both as a laser-cooled coolant means and as an ion temperature probe means. In the prior art, a large detuning frequency (preferably much larger than the natural linewidth) is required to obtain sufficient laser-cooling efficiency over a wide temperature range. On the other hand, small detuning frequency (preferably smaller than the natural linewidth) is required to obtain a strong signal intensity (change of fluorescence intensity). These two conflicting conditions are the cause of the issues of the prior art. This present invention resolves these mutually conflicting conditions, by providing independent and isolated means for the laser-cooling coolant and the ion-temperature probe.

Hereafter, a detailed description of the invention is given. First of all, a method for effectively selecting the laser cooling conditions is explained.

In order to increase the change of the fluorescence intensity of the ion-temperature probe after analysis heating, ion temperature before analysis should preferably be set to a low temperature below 1 K. However, if the temperature is too low (below 0.1 K), ion crystallization may occur, so that the oscillation frequency may differ from the secular motion frequency, which complicates data analysis. To simplify the analysis, a gaseous phase of ion should be preferably achieved by a balance between the laser cooling and heating, for which heating, typically, a trapping-radio-frequency heating effect is dominant in the absence of analysis heating. A large detuning frequency of −100 MHz or more, which is much larger than the natural linewidth of the transitions presently used, is utilized for the laser-cooling beam to achieve a gaseous phase within temperature 0.5 K to 1 K. The laser intensity is set to a saturated intensity with saturation parameter $\Omega_{Rabi}/\Gamma \approx 1$ to 5. For effective probing, the laser beam for the probe light should preferably have a detuning frequency much smaller than the natural linewidth, preferably in the vicinity of 0 MHz ($\Delta\nu = -20$ MHz to 20 MHz: optimized at 0 MHz), and its intensity should preferably set below the saturation intensity (saturation parameter: from approximately $\Omega_{Rabi}/\Gamma = 0.1$ to 1).

Two methods for separating the laser cooling means and the ion temperature probe means are explained next.

Method (1): A method with separate ion species for the laser cooled ions and the probe ions.

In this method, separation of the laser cooled means and the ion probe means are realized by using two ion species each supporting their respective function. To obtain strong laser-cooling, one ion species, which can be laser-cooled, is used as the laser-cooled ion using a saturating laser light with a large detuning frequency. To generate probe fluorescence, another ion species, which is able to be laser-cooled, is used as the probe ion, by utilizing a weak laser light in the vicinity of the 0 MHz detuning frequency. Effective operation can be attained within the natural width, typically at approximately $\Delta\nu = -20$ MHz to 20 MHz; however, 0 MHz is optimal, so that one can monitor the changes in fluorescence due to analysis heating of the sample ions.

It is effective to use two different isotopes of the same element as the two species of atomic ions for the laser cooled ions and the probe ions. In such a case, the two fluorescence wavelengths will be nearly identical. By using a method such as adding the laser intensity modulation to the probe light and then extracting the fluorescence intensity components synchronized with that modulation, only the fluorescence emitted by the probe ions can be monitored. For instance, by generating probe light intermittently with an optical chopper, the fluorescence intensity emitted by the probe ions will be detected only when the probe light is On.

Method (2): A method using a single ion species and two laser beams, one for a laser cooling means and the other for a probing means.

The separation of the laser cooling means and the probing means can be realized by using at least two laser beams to excite single species of laser-coolable ions to be used both as a coolant and a probe. One laser beam is used as a laser cooling means providing a saturating laser light at a large detuning frequency. Another laser light is used as a probe means providing a weak laser light substantially at a detuning frequency of zero (0). Fluorescence generated by the probe light is monitored.

The laser-cooling beam saturates the cooling transition of the ions. This saturation will affect the fluorescence excited by the probe beam. This reduces the ability of the probe beam to detect the ion temperature. Following two methods are effective in avoiding this deterioration in the ability to monitor ion temperature. In one method, the energy level used in laser cooling and the energy level used in the probe are separated. Separating these energy levels means that effects on probe light saturation can be avoided. In the other method, the laser-cooling light and the probe light excite the same level, but the laser-cooling light is stopped during observation of the fluorescence from the probe light. One example of achieving this intensity modulation is to use an optical chopper on the laser-cooling beam, so that one detects the fluorescence by the probe light when the cooling beam is off.

DESCRIPTION OF THE PREFERRED EMBODIMENTS

Embodiment I

Figure 1:
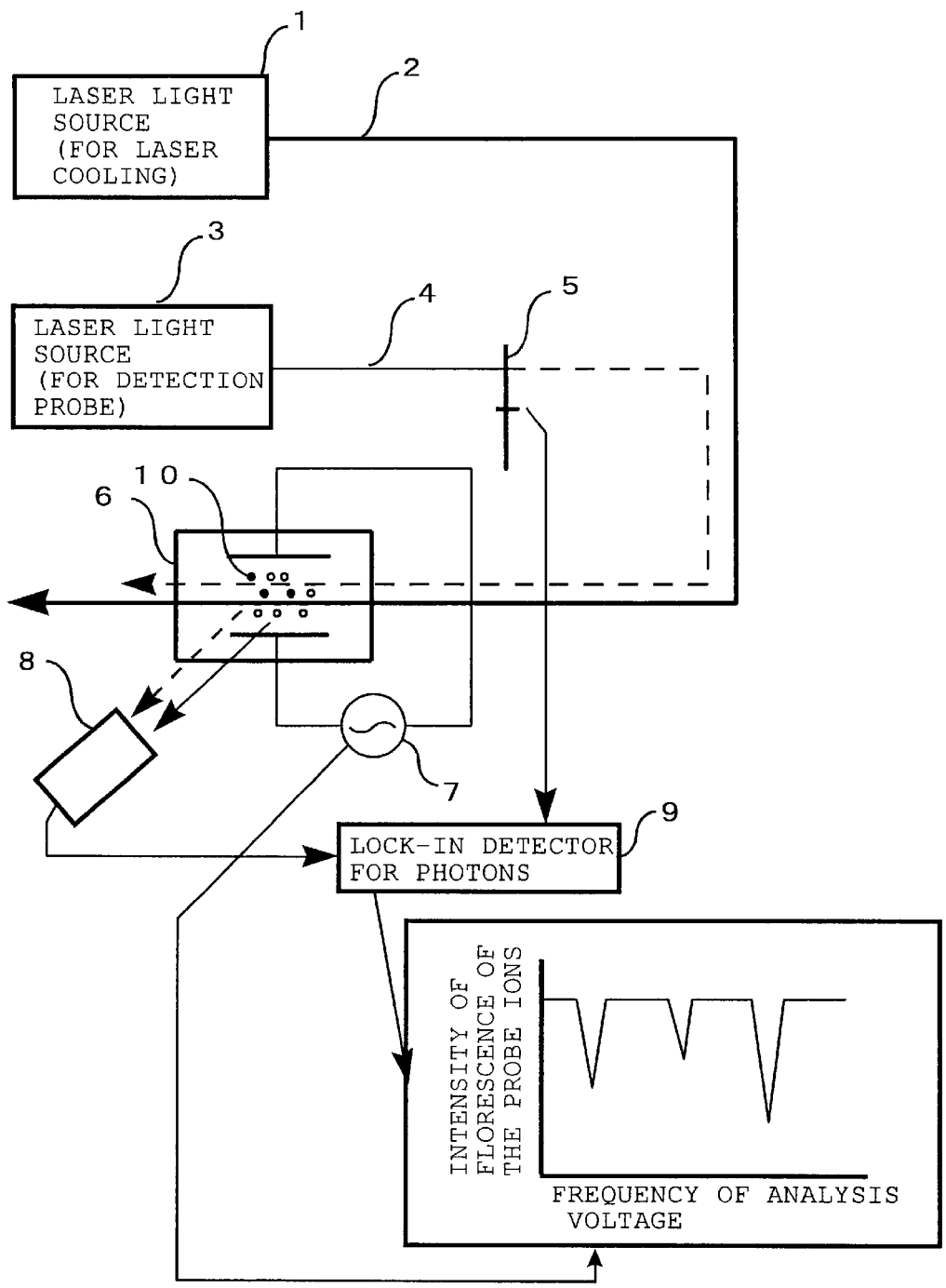
FIG. 1 is a block diagram showing the concept of the apparatus in one embodiment of this invention, where the laser-cold ions and probe ions are separate.
Figure 2:
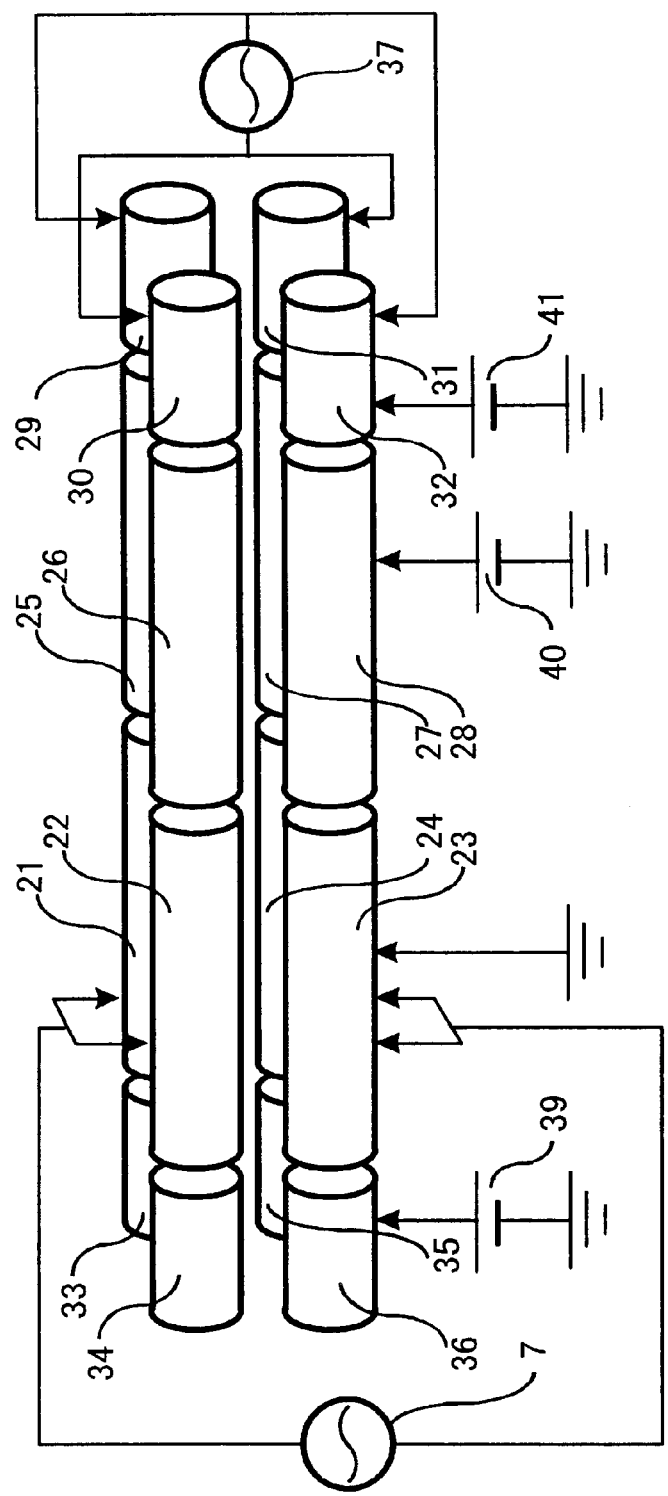
FIG. 2 is drawing illustrating the concept of the linear ion trap utilized in FIG. 1.

FIG. 1 and FIG. 2 shows a description of an embodiment of the present invention, where the laser cooled ions and the probe ions are different as explained above in Method (1). The laser-cooled ion used in this embodiment is $^{24}Mg^+$, and the probe ion is $^{26}Mg^+$. The natural abundance ratio of magnesium isotope is approximately $^{24}Mg^+:^{25}Mg^+:^{26}Mg^+$= 8:1:1.

Figure 15:
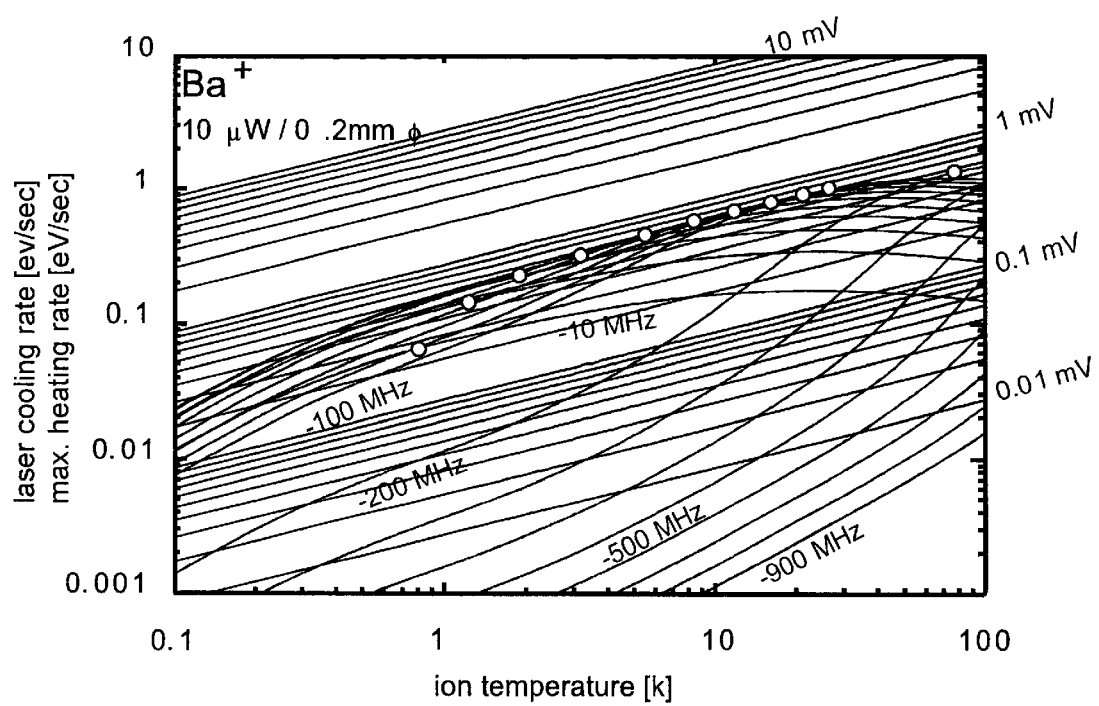
FIG. 15 is a graph showing calculated results when the laser beam intensity is 10 μW. Other conditions are the same as in FIG. 14.
Figure 16:
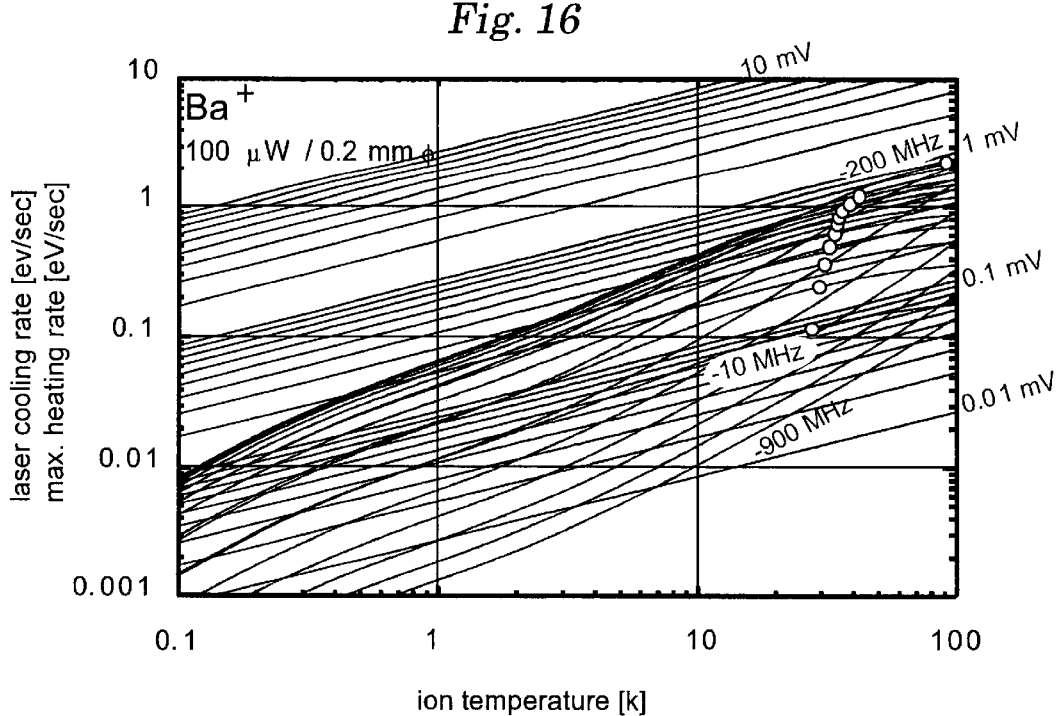
FIG. 16 is a graph showing calculated results when the laser beam intensity is 100 μW. Other conditions are the same as in FIG. 14.
Figure 17:
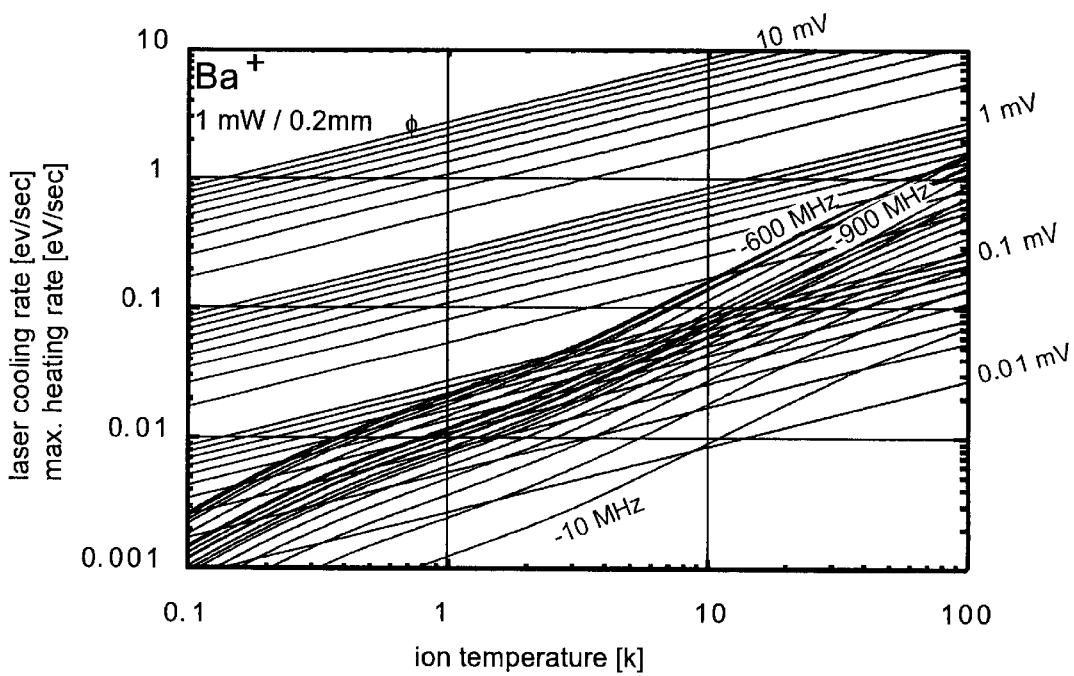
FIG. 17 is a graph showing calculated results when the laser beam intensity is 1 mW. Other conditions are the same as in FIG. 14.

FIG. 1 is a block diagram illustrating the structure of the apparatus of the embodiment. A radio-frequency-quadrupole linear ion trap shown in FIG. 2, which is placed inside an ultra-high vacuum chamber, is utilized as the ion trap means 6. The linear ion trap comprises the four electrodes 21 through 24 that have a hyperbolic cross section. In this embodiment, the electrode group 25 through 28, which have equivalent shape as the linear ion trap, is used as an ion source section. The end electrode groups 29 through 32, and 33 through 36 are installed at the ends to which direct current voltages 39, 41 are applied to prevent the ions from leaking out of the electrode ends. A direct current voltage 40 is further applied to the ion source section to prevent ions from leaking out of the ion trap. In this embodiment, the electrode structure on the end section is a linear quadrupole structure. Ions can be trapped along the axis of the electrodes by applying a radio-frequency-quadrupole voltage to these electrodes by a power supply 37. A specific example of this ion trap is found in the previously mentioned U.S. Pat. No. 5,679,950 relating to the application submitted by the inventors of the current application, where FIG. 15 of U.S. Pat. No. 5,679,950 give a detailed explanation and drawings.

In the following explanation, the electrode diameter of the ion trap electrodes is designated as $r_0$, When a radio frequency quadrupole voltage V having a frequency Ω, is applied to the electrodes 21 through 24 of the linear ion trap and the electrodes 25 through 28 of the ion source section, in the absence of DC quadrupole component, the radio frequency field φ, can be described by;

$$\phi = \frac{V\cos(\Omega t)(x^2 - y^2)}{2r_0^2} \qquad \text{(Equation 13)}$$

The equation of motion of the ions within the plane perpendicular to the ion trap axis is;

$$mx'' = \frac{eV\cos(\Omega t)x}{r_0^2} \qquad \text{(Equation 14)}$$

$$my'' = \frac{-eV\cos(\Omega t)y}{r_0^2}$$

This equation of motion is the Mathieu equation. By using the parameter q, and the normalized time ξ, such that;

$$q = \frac{2eV}{m\Omega^2 r_0^2} \qquad \text{(Equation 15)}$$

$$\xi = \frac{\Omega t}{2}$$

We obtain a variation of the standard Mathieu equation;

$$\frac{d^2 x}{d\xi^2} - 2q\cos(2\xi)x = 0 \quad \text{(Equation 16)}$$

$$\frac{d^2 y}{d\xi^2} - 2q\cos(2\xi)y = 0$$

To discuss the stability of trapped ions, in the absence of DC quadrupole field, the parameter q is used. Stable condition is realized when q is less than 0.908. When q is 0.5 or less, motion of trapped ions can be approximated by harmonic oscillation known as secular motion. Particularly, when no DC voltage is applied, the equation of motion is;

$$x'' = \frac{-\Omega^2 q^2 x}{8} \quad \text{(Equation 17)}$$

This motion is called secular motion, and its frequency $\omega$, which is called secular frequency is given by;

$$\omega = \frac{\Omega q}{2\sqrt{2}} \quad \text{(Equation 18)}$$

In this embodiment, $^{24}Mg^+$ and $^{26}Mg^+$ ions are respectively used as the laser cooled ions and the probe ions. Conditions of radio frequency are chosen so as to stably trap these ions at approximately q=0.2. Conditions for stable trapping can be achieved, for example, by approximately V=40 volts and $\Omega/2\pi$=3 MHz when $r_0$ equals 3 mm.

As stated previously, by applying a direct current voltage on the ion trap electrodes using the direct current power supplies 39 through 41, the leakage of ions from the electrode edges can be prevented and ions can be accumulated in the ion trap sections 21 through 24.

Mass-spectrometric analysis can be implemented by measuring the secular frequency $\Omega$ of the sample ions in the laser-cooled fluorescence mass spectrometry. An AC voltage of approximately 1 millivolt is applied between two adjacent pairs of linear ion trap electrodes consisting of a set of electrodes 21, 22 and a set of electrodes 23, 24 by utilizing a mass-analysis power supply 7 composed of a power supply where the frequency can be swept. Using this power supply voltage, a dipole electrical field within the ion trap is created to resonantly oscillate the sample ions, and forced-oscillation heating of the cooled ions is performed.

The respective resonance wavelength of the $^{24}Mg^+$ laser-cooled ions and the $^{26}Mg^+$ probe ions utilized in this embodiment is around 280 nm. The laser light source 1 in the figure is for laser cooling of the $^{24}Mg^+$ ions, which is achieved, for example, by a dye laser pumped by an argon ion laser and equipped with a second harmonic generation crystal such as a KDP crystal. The laser light source 3 in the figure is for generating probe laser light to excite fluorescence of the $^{26}Mg^+$ probe ions, and can be achieved by a laser comprising the same structure as the laser-cooling laser. The respective wavelengths emitted however are different slightly. Since detailed description of the process of laser cooling of the $^{24}Mg^+$ ions is well known and reported in many research studies, we omit its explanation. The reference numerals 2 and 4 are lines showing the laser beam outputs from the respective laser light sources. Reference numeral 5 is a chopper for making chopping the laser light 4 periodically. A broken line is shown downstream the chopper 5 in the figure to signify intermittent emission of the laser light 4. A mechanical optical chopper may be used as the chopper 5, or alternatively, the optical path of the light can be regulated by means of an acousto-optical modulator to perform intermit control of the incoming light beam to the ion trap means 6. Reference numeral 8 is an photomultiplier tube and detects the fluorescence of the $Mg^+$. Reference numeral 10 shows ions trapped in the ion trap means 6 such as laser cooled ions, probe ions and sample ions.

The fluorescence, which is shown by the solid and broken lines in the figure, from the laser cooling light 2 and from the probe light 4 is detected by a photomultiplier tube 8. On/off modulation of the probe light 4 is achieved by the optical chopper 5. The fluorescence component synchronized with the on/off operation of the optical chopper 5 is extracted by a lock-in detector for photons 9, so that the fluorescence emitted by the $^{26}Mg^+$ probe ions is extracted out of the total detected fluorescence. The inset shows a schematic figure of a typical data, with the frequency of the analysis voltage taken along the horizontal axis, and the fluorescence intensity of the probe ions is taken along the vertical axis.

Mass-spectrometric analysis starts with the loading of ions into the trap. In this embodiment. The magnesium vapor enters the ion source sections 25 through 28 where the ions are generated by electron impact. A display of atomic oven, atomic beam, the electron beam, electron beam power supply is omitted from the figure. The sample gases are also introduced into the ion source section 25 through 28 in a similar manner and are ionized. Next, $^{24}Mg^+$ is laser-cooled by the laser light 2. Some cooling period is required for the sample ions and the probe ions to be sympathetically cooled, according to the effects of the $^{24}Mg^+$ laser cooling. On reaching equilibrium, the fluorescence emitted by $^{24}Mg^+$, and the fluorescence emitted by $^{26}Mg^+$ is observed, and the equilibrium is confirmed by the lack of temporal variations of the fluorescence intensity. The laser-cooling beam conditions are set for the 24Mg$^+$ laser-cooled ions, so that strong laser-cooling with a large detuning frequency, typically larger than the natural linewidth, is realized for stable cooling. Next, a probe light 4 with a detuning frequency much smaller than the natural linewidth, or substantially 0 MHz, is radiated on the $^{26}Mg^+$ ions.

After above operation, mass-spectrometry analysis is performed. The analysis voltage 7 is applied with a frequency sweep, the chopper 5 turns the probe beam 4 on and off, and the fluorescence intensity emitted by the probe ions is monitored when the probe light 4 is on.

Figure 6:
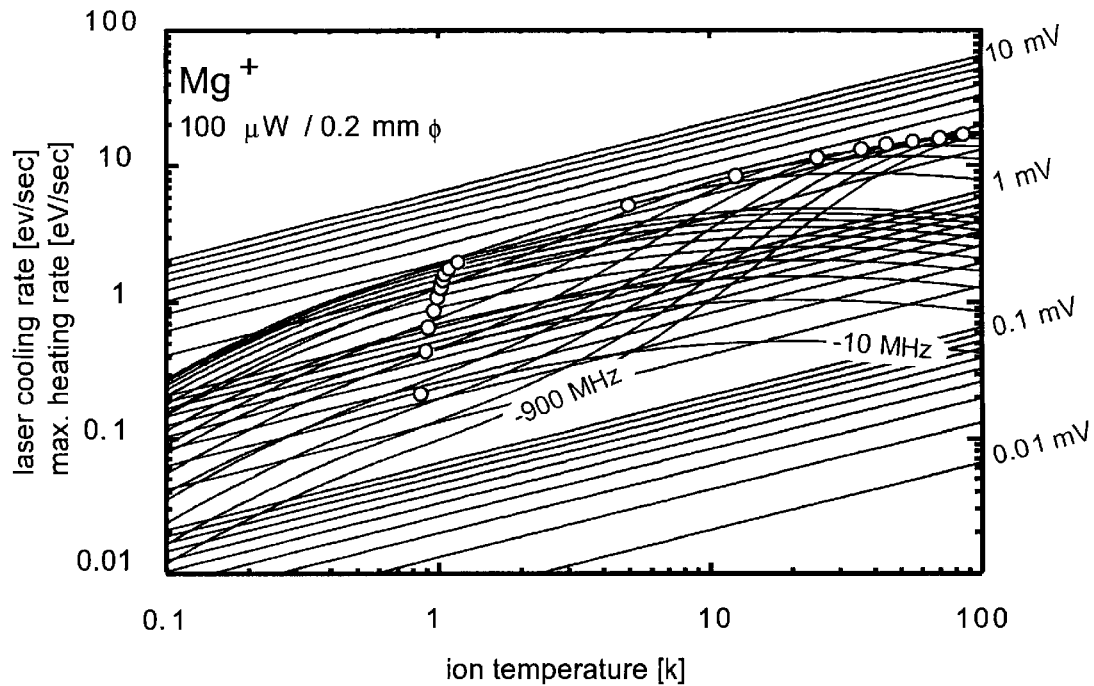
FIG. 6 is a graph showing calculated results when the laser beam intensity is 100 μW. Other conditions are the same as in FIG. 4.
Figure 7:
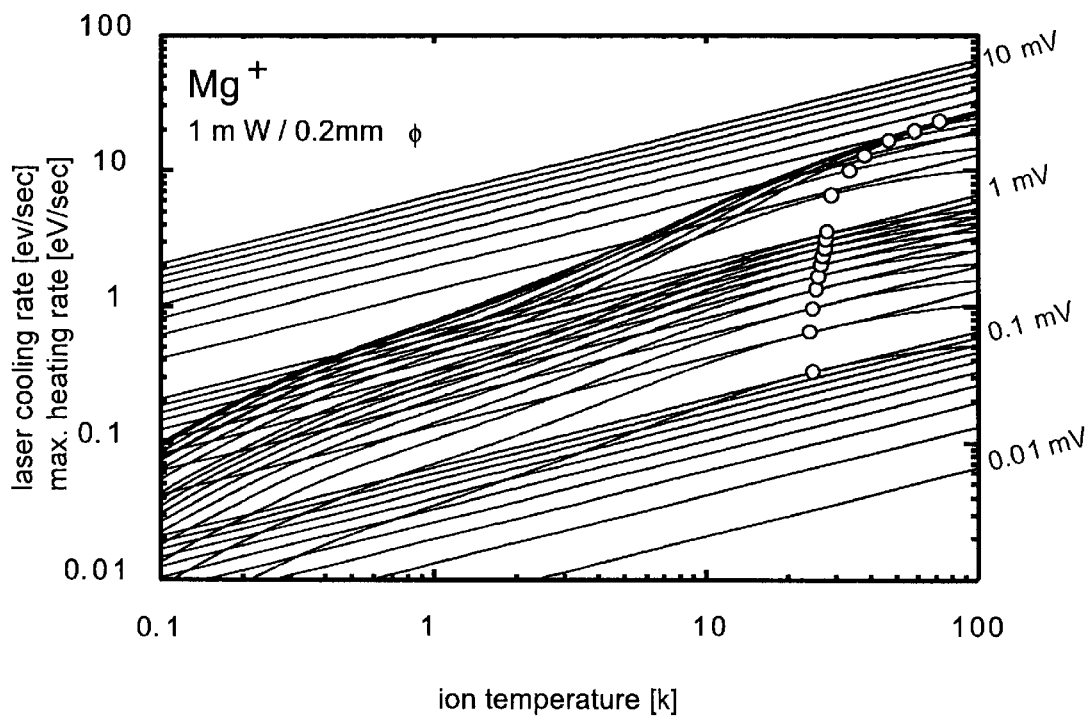
FIG. 7 is a graph showing calculated results when the laser beam intensity is 1 mW. Other conditions are the same as in FIG. 4.
Figure 8:
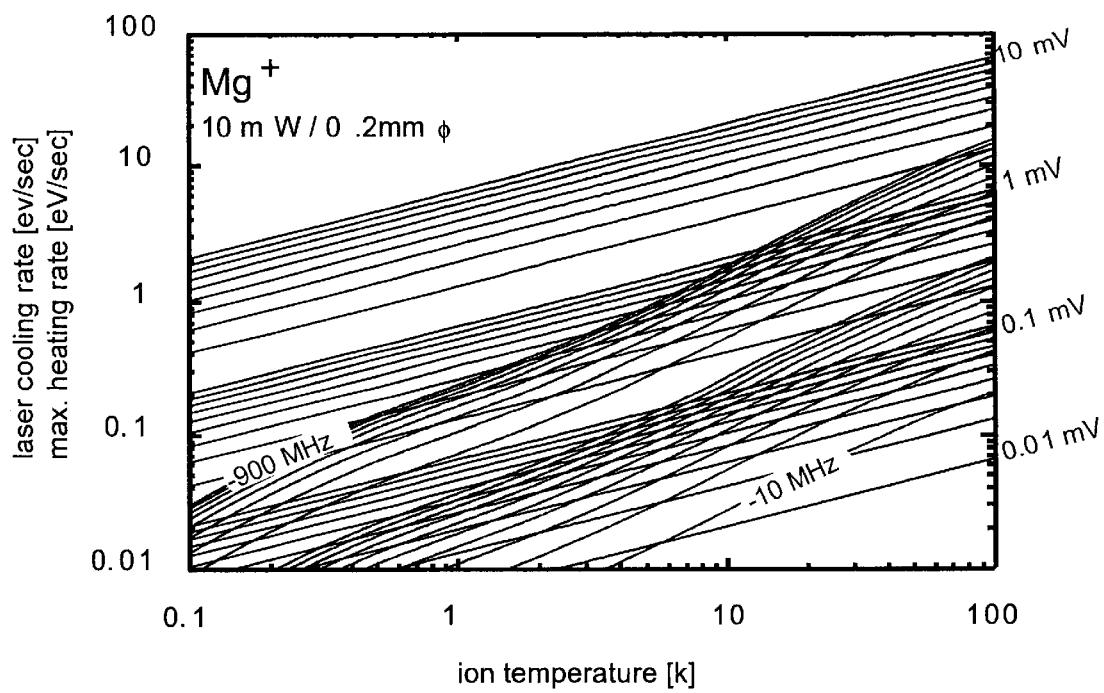
FIG. 8 is a graph showing calculated results when the laser beam intensity is 10 mW. Other conditions are the same as in FIG. 4.
Figure 9:
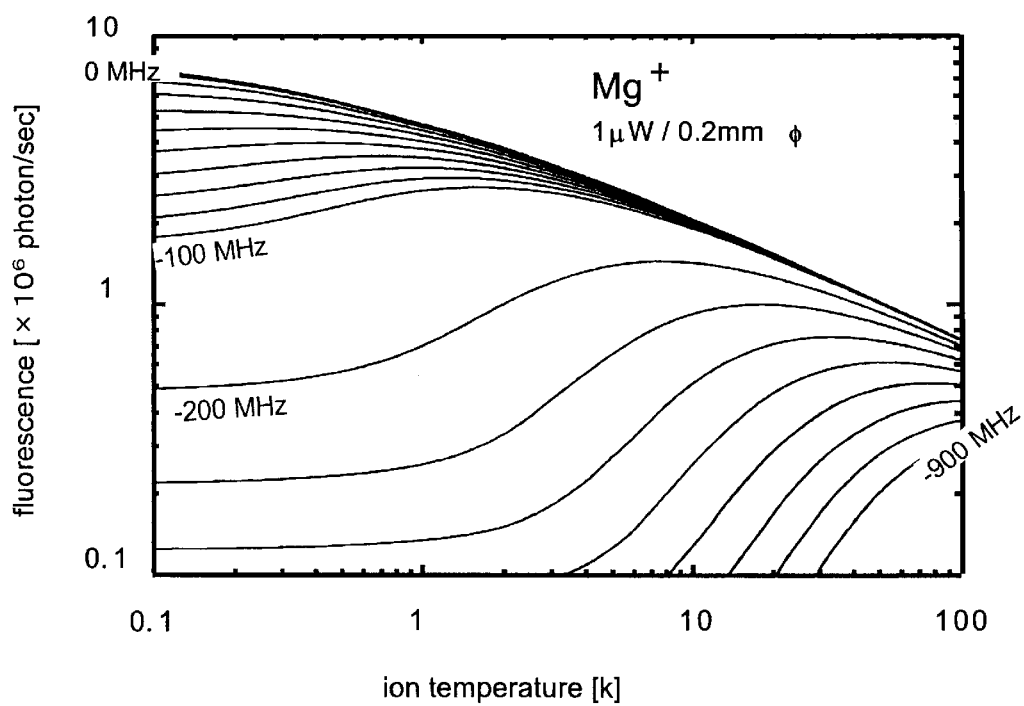
FIG. 9 is a graph showing calculated results of the relation between fluorescence intensity and ion temperature, where the laser-cooled ions are magnesium ions, the laser beam is focused to 0.2 mm, and the laser beam intensity is 1 μW.
Figure 10:
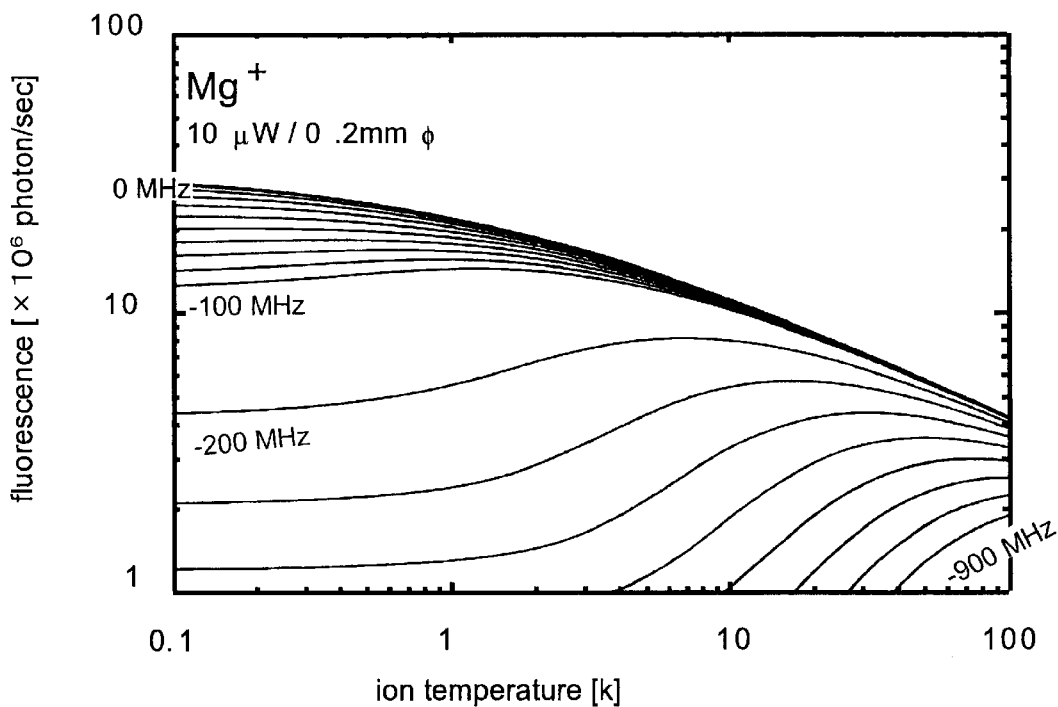
FIG. 10 is a graph showing calculated results when the laser beam intensity is 10 μW. Other conditions are the same as in FIG. 9.
Figure 11:
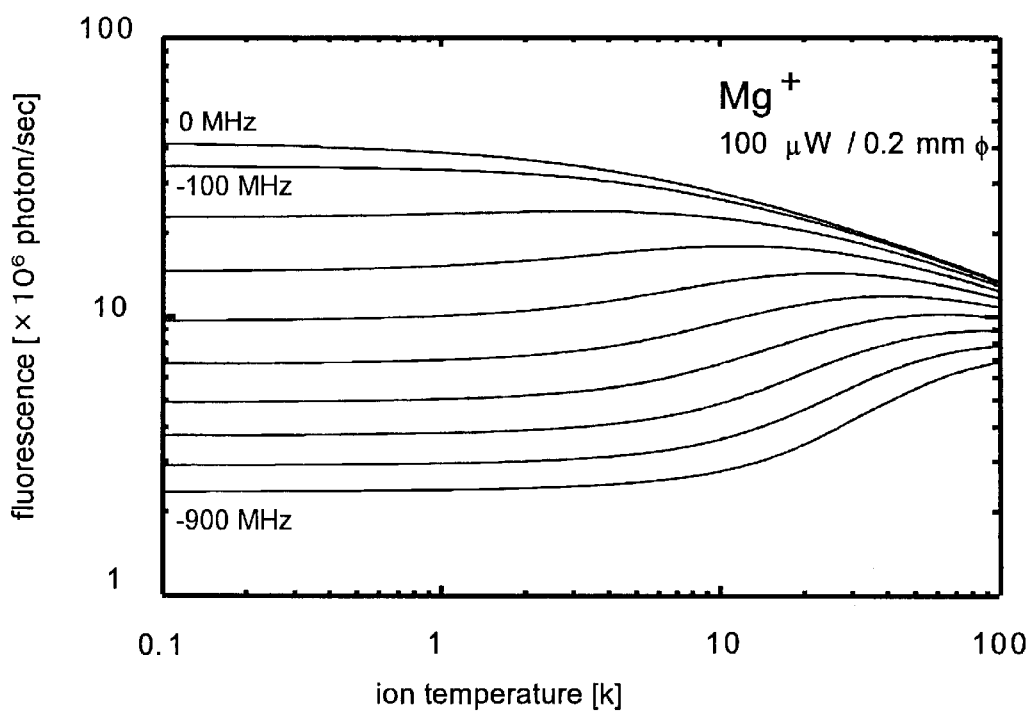
FIG. 11 is a graph showing calculated results when the laser beam intensity is 100 μW. Other conditions are the same as in FIG. 9.
Figure 12:
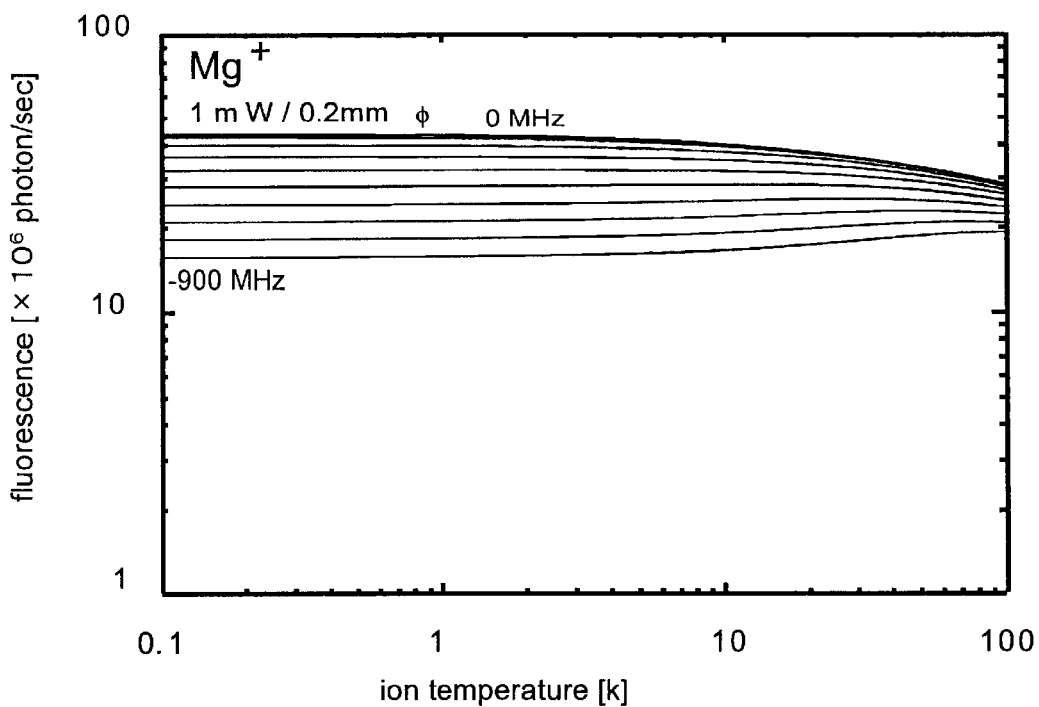
FIG. 12 is a graph showing calculated results when the laser beam intensity is 1 mW. Other conditions are the same as in FIG. 9.
Figure 13:
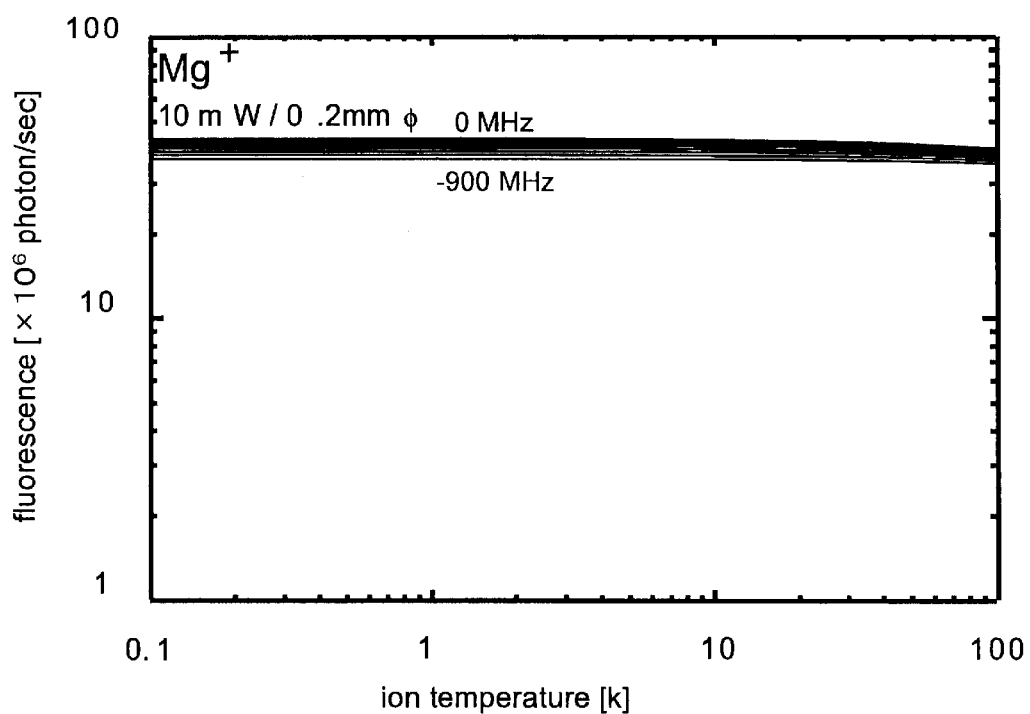
FIG. 13 is a graph showing calculated results when the laser beam intensity is 10 mW. Other conditions are the same as in FIG. 9.
Figure 14:
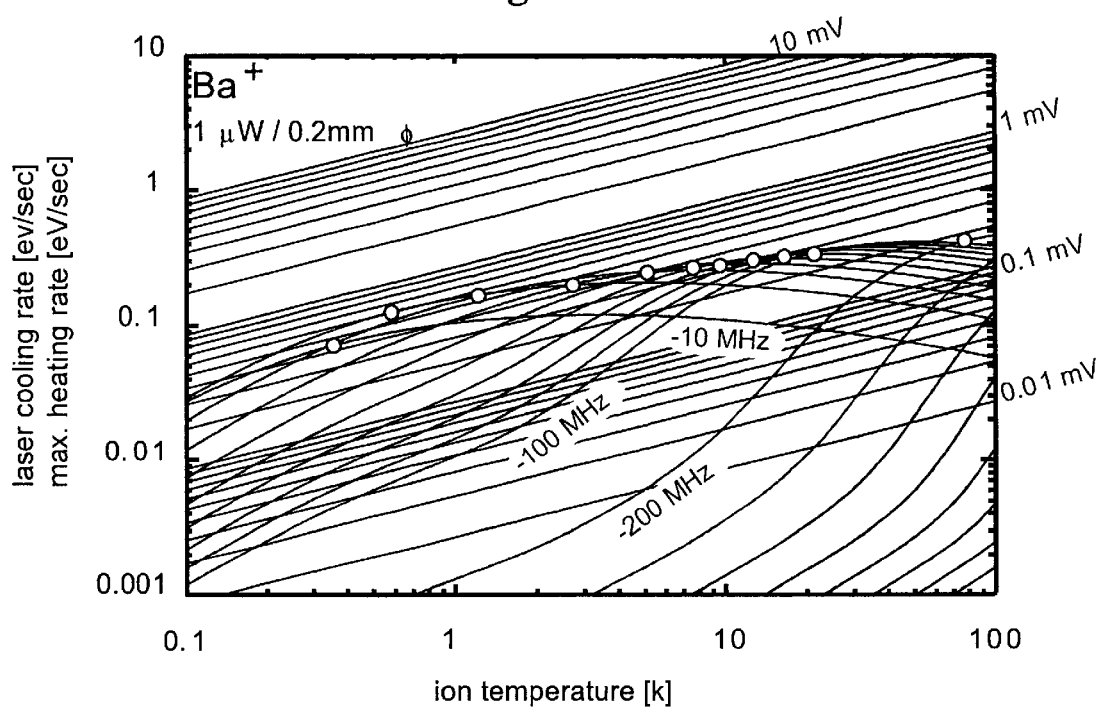
FIG. 14 is a graph showing calculated results of the laser-cooling rate and the maximum heating rate provided by an analysis voltage, where the laser-cooled ions are barium ions, the laser beam is focused to 0.2 mm, and the laser beam intensity is 1 μW.
Figure 22:
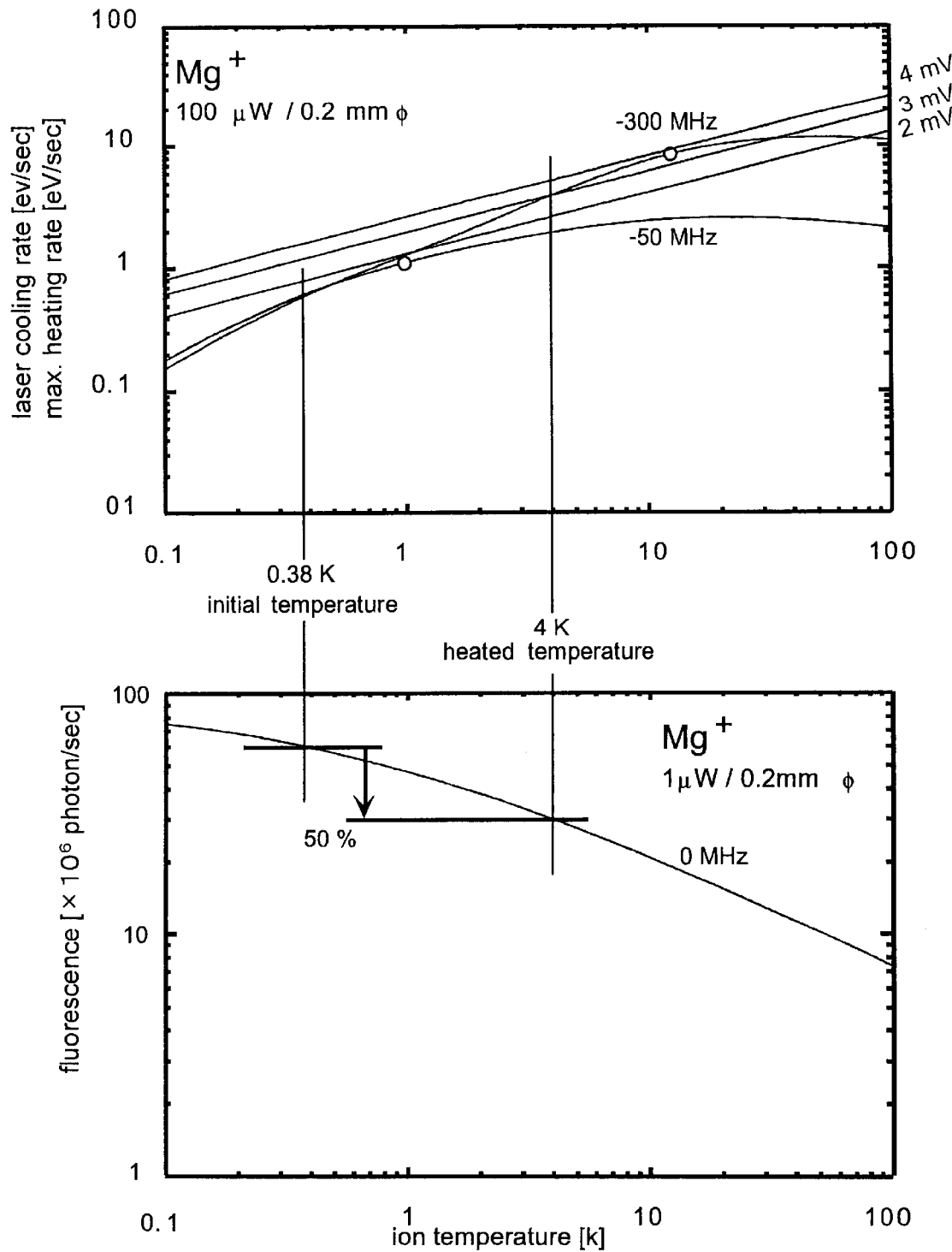
FIG. 22 is a graph illustrating selection of the laser parameters in the first embodiment shown in FIG. 1.

Laser parameters for performing analysis are selected as previously explained, but a detailed example will be described here. In the embodiment of the prior art, a laser-cooled fluorescence mass spectrum was obtained when $^{24}Mg^+$ ions were laser-cooled at a detuning frequency of −50 MHz and with a laser intensity of 100$\mu$ watts, in which the ion temperature was measured to be 0.38 K prior to analysis. In a saturated state with a laser intensity of 100$\mu$ watts, FIG. 6 and the upper diagram of FIG. 22 show that allowable detuning frequencies for stably obtaining 0.38 K are −50 MHz and −300 MHz, as calculated following the approximation already explained. At −50 MHz, the maximum attainable ion temperature (shown by white circles in FIG. 6 and FIG. 22) is 1 K, but at −300 MHz, the maximum attainable ion temperature is approximately 10 Kelvin. However, if one uses a probe light for $^{26}Mg^+$ excitation with 100$\mu$ watts intensity and a detuning frequency of substantially 0 MHz, then the ion temperature is calculated to reach 4 Kelvin, as shown in the lower figure of FIG. 22, resulting in a fluorescence intensity decrease of 50 percent compared to the fluorescence at the initial temperature of 0.38 Kelvin. According to FIG. 22, at a detuning frequency of −50 MHz, this temperature exceeds the maximum attainable ion temperature 1 Kelvin, so that it is not achieved stably. At the detuning frequency of −300 MHz, this can be stably achieved, and further, there is an ample margin up to the maximum attainable temperature of 10 Kelvin. An ion temperature of 4 Kelvin at the time of analysis heating could be achieved by applying approximately 3 mV as the analysis voltage amplitude $V_{ac}$. By selecting the analysis parameters as described in this method, it is possible to realize more stable mass analysis where ions are less likely to be lost than in the method of the prior art.

Embodiment II

An embodiment is next described utilizing barium ions, $Ba^+$, as the laser-cooled ions in the method previously described in Method (2), where a laser-cooling light and another probe light with different wavelengths are radiated onto one species of laser-cooled ion. In the explanation of the embodiment here in particular, the laser-cooling transition and the probe transition are set the same, and modulation of the laser-cooling light intensity is performed utilizing an optical chopper to avoid the effects of saturation on the probe light.

Figure 3:
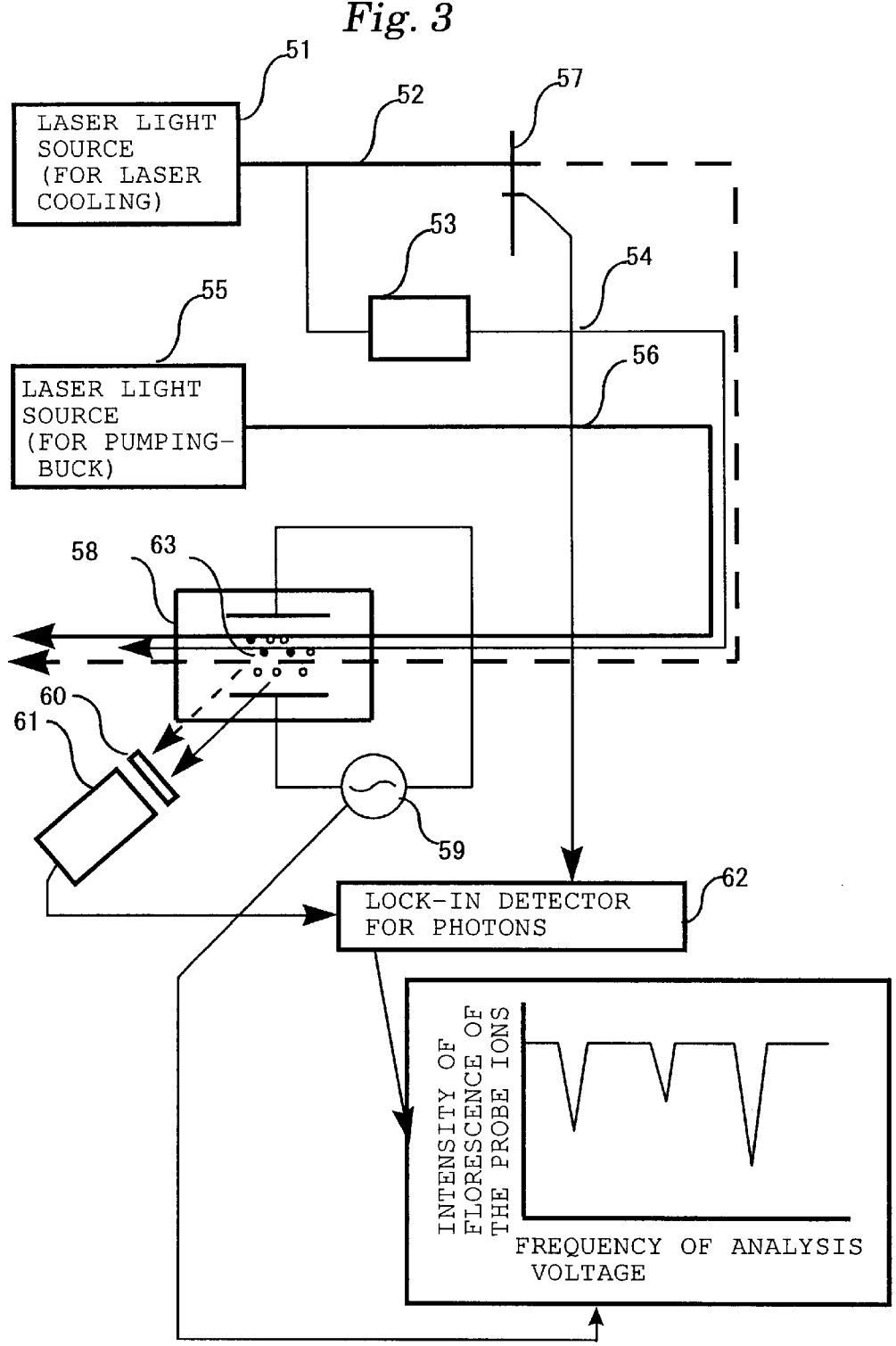
FIG. 3 is a block diagram showing the concept of a typical apparatus in another embodiment of this invention, where laser-cooling light and probe light of two wavelengths are applied on one species of laser-coolable ion.
Figure 4:
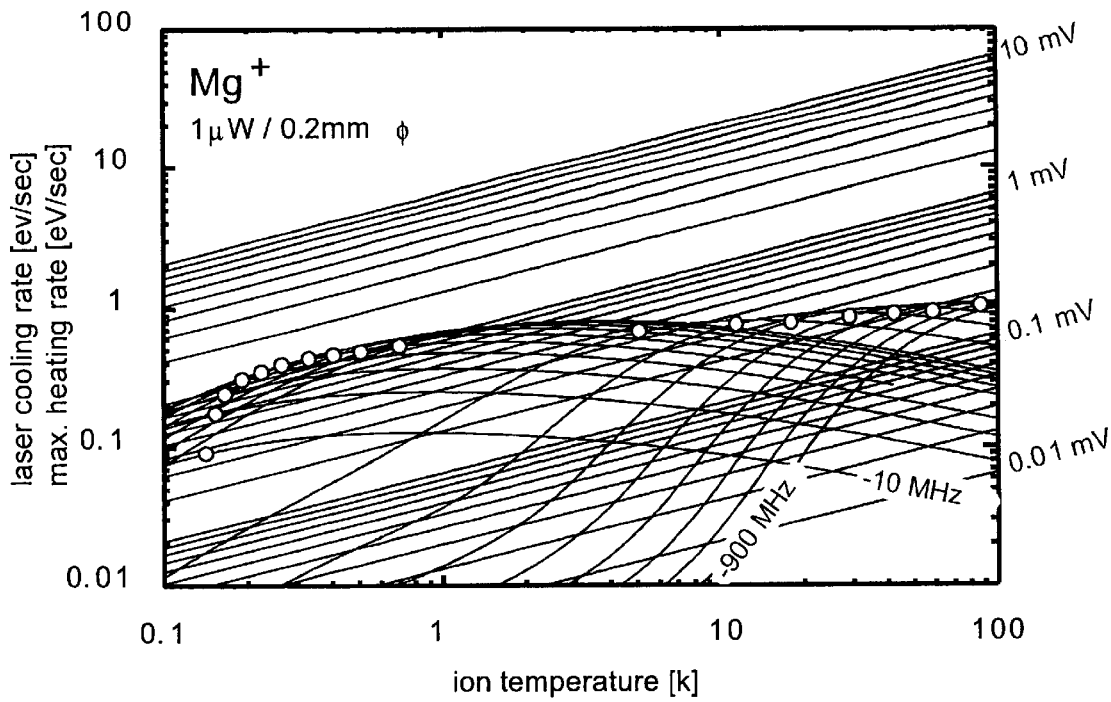
FIG. 4 is a graph showing calculated results of the laser-cooling rate and the maximum heating rate provided by an analysis voltage, where the laser-cooled ions are magnesium ions, the laser beam is focused to 0.2 mm, and the laser beam intensity is 1 μW. Calculations are performed for detuning frequencies −10, −20, −30, −40, −50, −60, −70, −80, −90, −100, −200, −300, −400, −500, −600, −700, −800, and −900 MHz.
Figure 5:
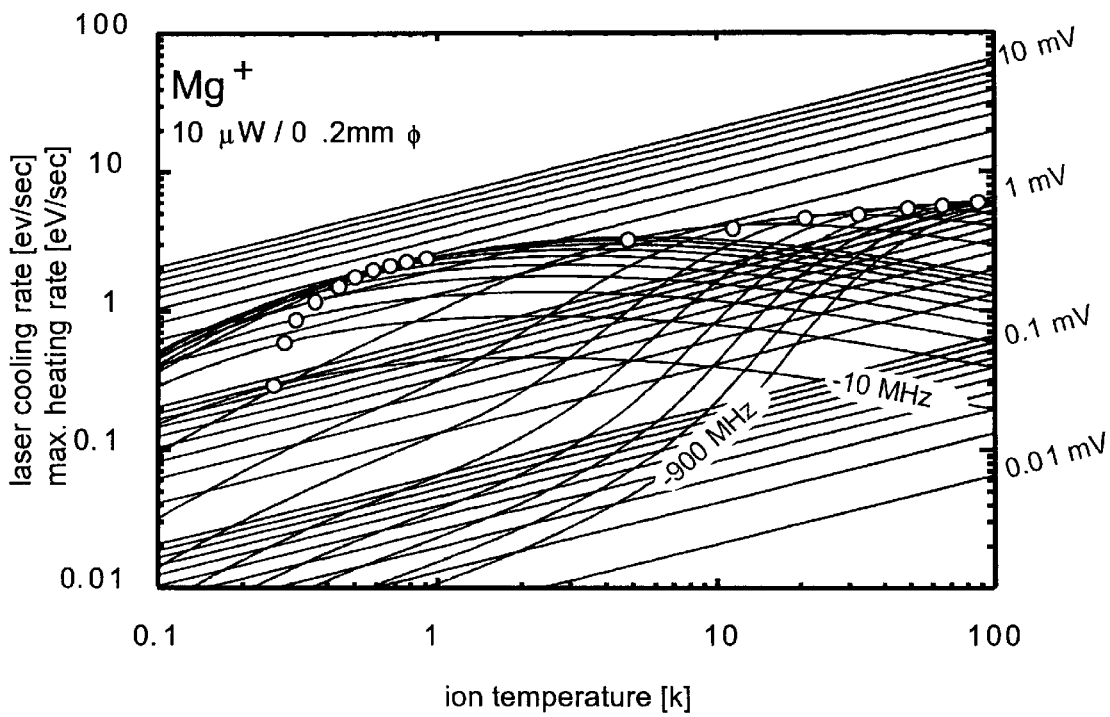
FIG. 5 is a graph showing calculated results when the laser beam intensity is 10 μW. Other conditions are the same as in FIG. 4.

The structure of the apparatus is shown in FIG. 3. The following points differ from the first embodiment. Two-color laser system is required for laser-cooling of barium ion $Ba^+$. An optical chopper 57 is installed to modulate the laser cooled light 52. No other species of ions are required for the probe. To acquire probe light, a portion of the laser-cooling light is put into an acousto-optical modulator 53, and the shifted frequency is used as the probe light. The apparatus is equivalent to the apparatus of the first embodiment, whose brief description follows. Reference numeral 58 is an ion trap means, 59 is a mass analysis power supply, 61 as a photomultiplier tube, 62 is a lock-in detector for photons, 63 designates laser cooling ions and sample ions. Each above mentioned components is respectively the same as the ion trap means 6, the mass analysis power supply 7, the photomultiplier tube 8, the lock-in detector for photons 9, and the laser cooled ions and sample ions 10. The reference numeral 60 here denotes an optical filter. This optical filter 60 is for eliminating noise photons caused by light emissions from the laser cooling ions and sample ions 63 due to the pumping-back laser light 56.

A two-color laser system is required for laser-cooling cooling of the barium ions $Ba^+$. One laser light is called laser-cooling light 52 at a wavelength of 493 nm and supplied from a laser light source 52. The other laser light is called the pumping-back light 56 at a wavelength of 650 nm supplied from the laser light source 55, which avoids effects of optical pumping to the quasi-stable level of $Ba^+$ ion. Since implementation of the laser-cooling of barium ions $Ba^+$ has already been published in papers on a large number of research studies in the known art, explanation is omitted here. Though dye lasers can be used for laser cooling of the barium ions $Ba^+$, semiconductor lasers allow laser cooling of barium ions $Ba^+$ more simply and at a lower cost (Reference 2).

In this embodiment, a portion of the laser cooling light 52 is frequency-shifted and used as the probe light 54. The amount of frequency shift is adjusted so that the frequency-shifted probe light 54 attains a detuning frequency of substantially zero MHz, that is, much less. than the natural linewidth. To achieve this, the amount of frequency shift is determined in reference to the optimal detuning frequency of the laser-cooling light. Since the laser cooling transition and the probe transition are the same, the probe fluorescence is subject to saturation effects due to intense laser-cooling light. Since the saturation effect lowers the sensitivity, the laser light 52 is modulated by the optical chopper 57, so that the fluorescence from the probe light is observed only when the laser-cooling light 52 is blocked.

Figure 18:
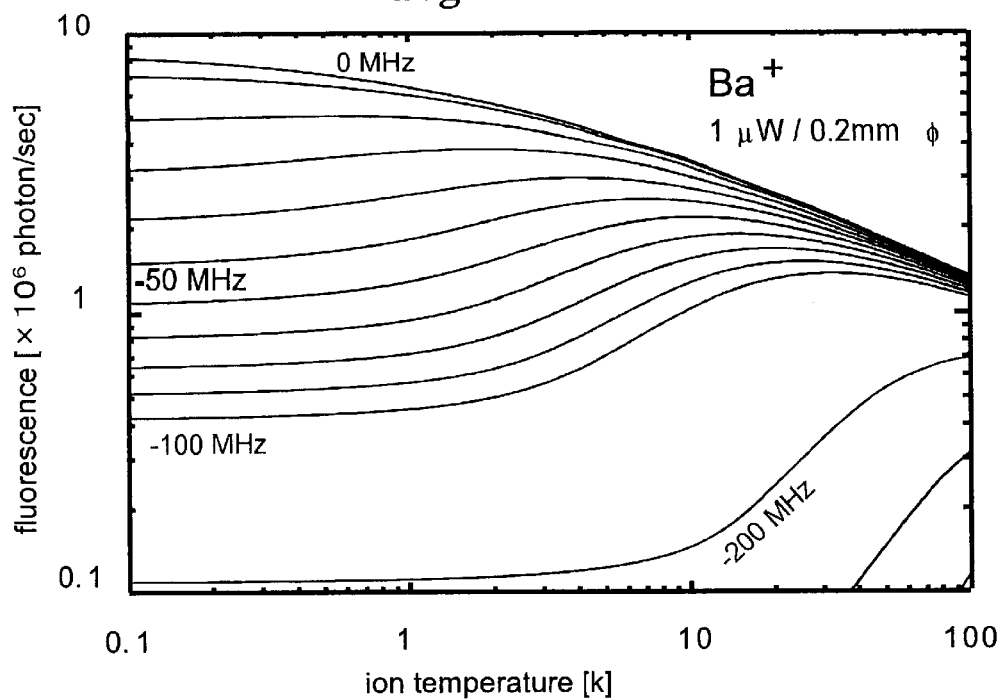
FIG. 18 is a graph showing calculated results of the relation between fluorescence intensity and ion temperature, where the laser-cooled ions are barium ions, the laser beam is focused to 0.2 mm, and the laser beam intensity is 1 μW.
Figure 19:
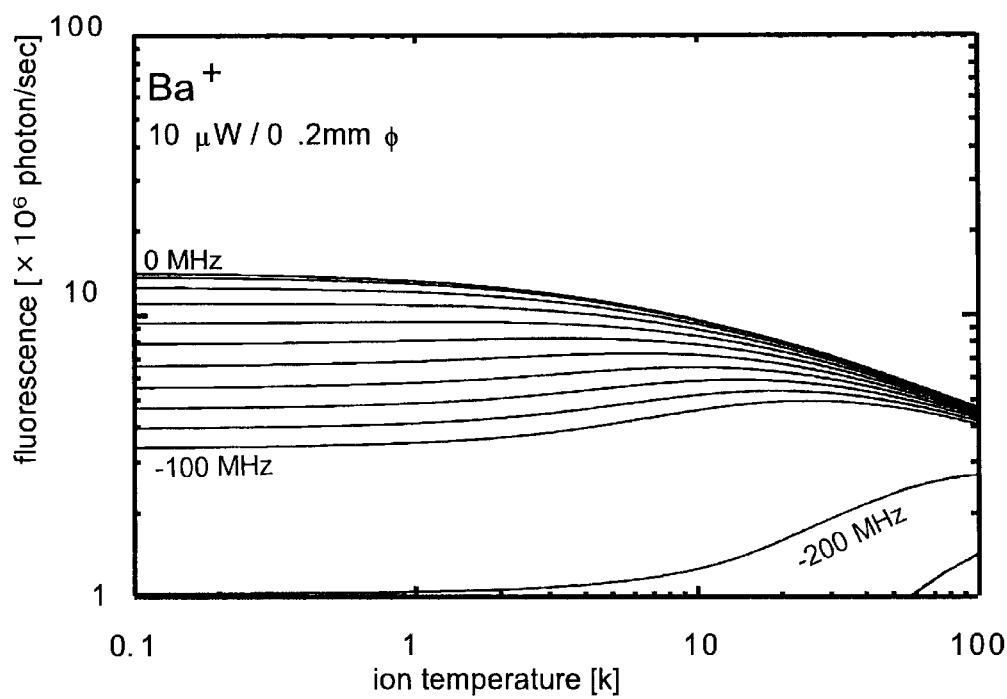
FIG. 19 is a graph showing calculated results when the laser beam intensity is 10 μW. Other conditions are the same as in FIG. 18.
Figure 20:
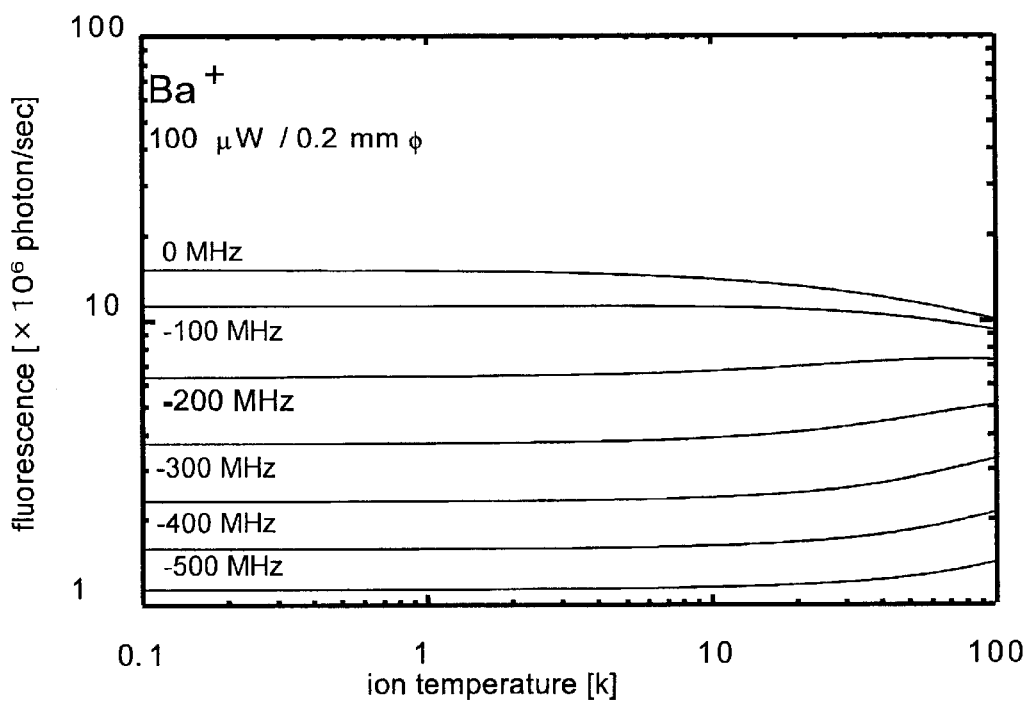
FIG. 20 is a graph showing calculated results when the laser beam intensity is 100 μW. Other conditions are the same as in FIG. 18.
Figure 21:
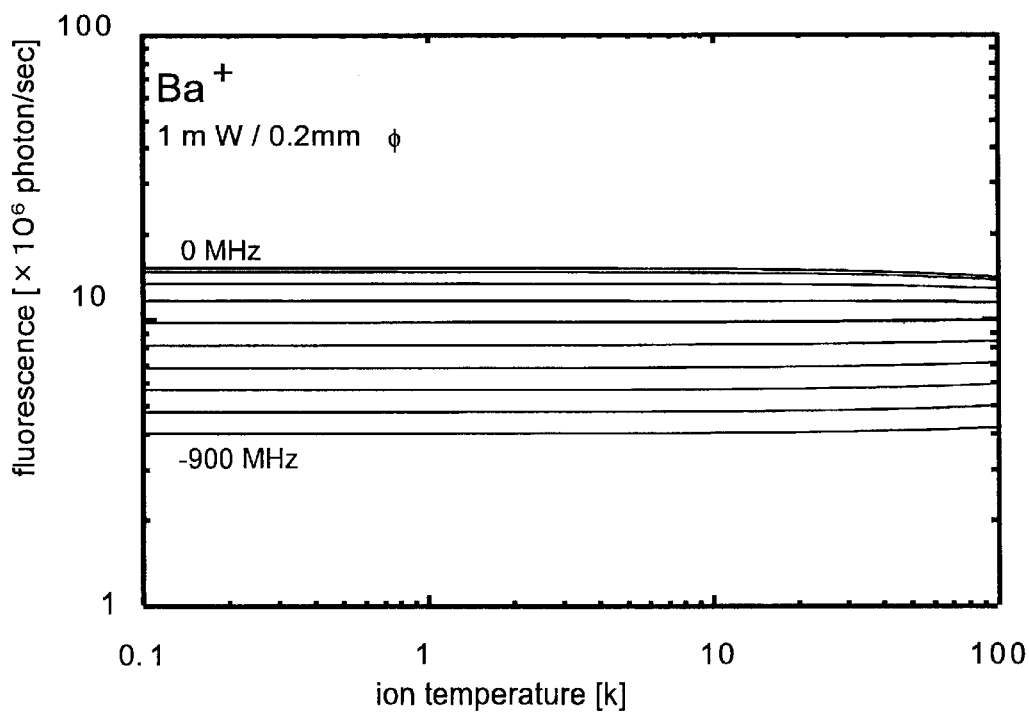
FIG. 21 is a graph showing calculated results when the laser beam intensity is 1 mW. Other conditions are the same as in FIG. 18.
Figure 23:
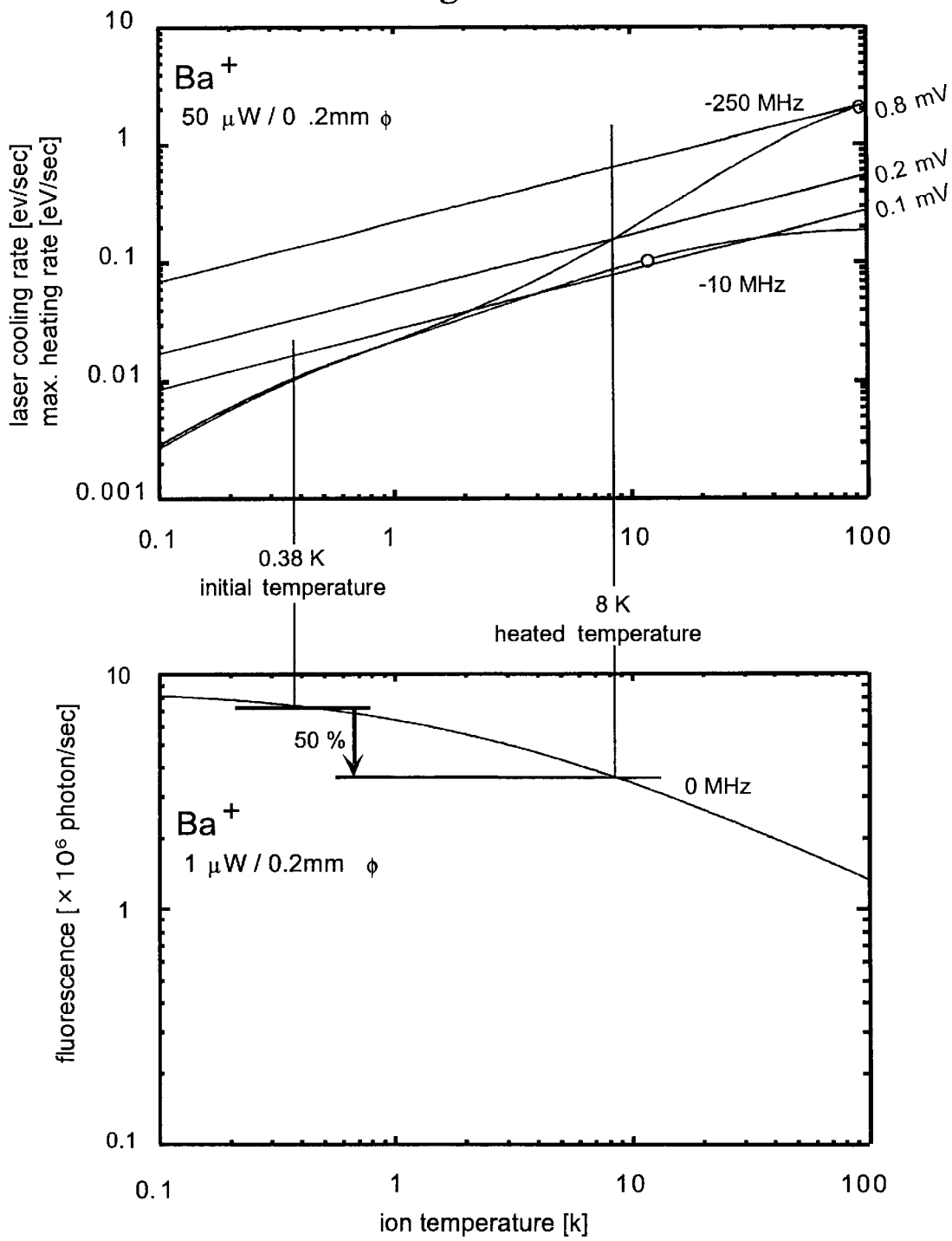
FIG. 23 is a graph illustrating selection of the laser parameters in the second embodiment shown in FIG. 3.

The selection of parameters when performing analysis is determined as previously described. In the embodiment of the prior art that utilized barium ions $Ba^+$, a mass spectrum was acquired at a laser intensity of $50\mu$ watts and at a detuning frequency of −10 MHz. FIG. 23 shows the laser-cooling characteristics for this intensity, which result is not included in FIG. 14 through FIG. 17. At a typical value of 0.38 K for the pre-analysis ion temperature, the laser cooling rate at −10 MHz detuning can be as well achieved at a detuning frequency of −250 MHz as shown in the upper figure of FIG. 23. When these parameters are selected for the laser light 52, the maximum ion temperature is about 100 K. For the probe beam 54, on the other hand, the detuning frequency is set to substantially 0 MHz, and the laser intensity is set to $1\mu$ watt, so that the transition will not saturate, while maximizing the fluorescence intensity. The temperature at which the fluorescence intensity decreases 50 percent with respect to a pre-analysis temperature of 0.38 K is calculated to be 8 K as shown in FIG. 18 and in the lower figure of FIG. 23. At −10 MHz detuning, there is a high probability of losing ions, since 8 K is almost equal to the maximum ion temperature during analysis. At a detuning frequency of −250 MHz, there is sufficient margin till reaching the maximum ion temperature, so that the probability of losing ions is greatly decreased. Applying an amplitude of 0.2 mV as the analysis voltage $V_{ac}$ will achieve an ion temperature of 8 K during analysis.

Since the operation procedure for mass analysis is identical to the procedure of the first embodiment, description is omitted here.

This invention as described above is therefore capable of improved laser-cooled fluorescence mass spectrometry.

What is claimed is:

1. A method of laser-cooled fluorescence mass spectrometry comprising the steps of:
    trapping sample ions, laser-cooled ions, and probe ions in an ion trap, the probe ions being different ions than the laser-cooled ions;
    irradiating the sample ions, the laser-cooled ions, and the probe ions in the ion trap with a first laser beam for cooling the ions;
    irradiating the sample ions, the laser-cooled ions, and the probe ions in the ion trap with a second laser beam for detecting temperature changes in the ions; and
    detecting the temperature changes in the ions.

2. A method of laser-cooled fluorescence mass spectrometry according to claim 1, wherein beam intensity modulation is applied to the second light beam, and the change in fluorescence of the probe ions is measured as the intensity modulation of the second laser beam.

3. A method of laser-cooled fluorescence mass spectrometry according to claim 1, wherein the detuning frequency of the laser beam which laser-cools the laser-cooled ions is set to a negative value, and the absolute value is larger than 100 MHz.

4. A method of laser-cooled fluorescence mass spectrometry according to claim 1, wherein the intensity of the laser beam which laser-cools the laser-cooled ions is set to a value so that the spectral width at the Rabi frequency becomes as large as or larger than the natural linewidth of the cooling transition.

5. A method of laser-cooled fluorescence mass spectrometry according to claim 1, wherein the detuning frequency of the laser beam which excites fluorescence of the probe ions is set to an absolute value smaller than 10 MHz.

6. A method of laser-cooled fluorescence mass spectrometry according to claim 1, wherein the intensity of the laser beam which excites fluorescence of the probe ions is set to a value so that the spectral width at the Rabi frequency becomes smaller than the natural linewidth of the probe transition.

7. A method of laser-cooled fluorescence mass spectrometry comprising the steps of:

trapping sample ions, laser-cooled ions, and probe ions in an ion trap, the probe ions being the same ions as the laser-cooled ions;

irradiating the sample ions, the laser-cooled ions, and the probe ions in the ion trap with a first laser beam for cooling the ions;

irradiating the sample ions, the laser-cooled ions, and the probe ions in the laser trap with a second laser beam for detecting temperature changes in the ions; and detecting the temperature changes in the ions.

8. A method of laser-cooled fluorescence mass spectrometry according to claim 7, wherein the detuning frequency of the laser beam which laser-cools the laser-cooled ions is set to a negative value, and the absolute value is larger than 100 MHz.

9. A method of laser-cooled fluorescence mass spectrometry according to claim 7, wherein the intensity of the laser beam which laser-cools the laser-cooled ions is set to a value so that the spectral width at the Rabi frequency becomes as large as or larger than the natural linewidth of the cooling transition.

10. A method of laser-cooled fluorescence mass spectrometry according to claim 7, wherein the detuning frequency of the laser beam which excites fluorescence of the probe ions is set to an absolute value smaller than 10 MHz.

11. A method of laser-cooled fluorescence mass spectrometry according to claim 7, wherein the intensity of the laser beam which excites fluorescence of the probe ions is set to a value so that the spectral width at the Rabi frequency becomes smaller than the natural linewidth of the probe transition.

12. A method of laser-cooled fluorescence mass spectrometry according to claim 7, wherein beam intensity modulation is applied to the laser cooling beam, and the change in fluorescence of the probe ions is measured when the intensity of the laser cooling beam is decreased by the modulation.

* * * * *